United States Patent
Dourlat et al.

(10) Patent No.: US 11,452,739 B2
(45) Date of Patent: Sep. 27, 2022

(54) POLYSACCHARIDES FOR THE TREATMENT OF OCULAR CONDITIONS

(71) Applicant: SANTEN SAS, Evry (FR)

(72) Inventors: Jennifer Dourlat, Boulogne-Billancourt (FR); Philippe Daull, Soisy-sur-Seine (FR); Jean-Sébastien Garrigue, Verrières le Buisson (FR)

(73) Assignee: SANTEN SAS, Evry (FR)

( * ) Notice: Subject to any disclaimer, the term of this patent is extended or adjusted under 35 U.S.C. 154(b) by 182 days.

(21) Appl. No.: 17/041,103

(22) PCT Filed: Mar. 26, 2019

(86) PCT No.: PCT/EP2019/057599
§ 371 (c)(1),
(2) Date: Sep. 24, 2020

(87) PCT Pub. No.: WO2019/185632
PCT Pub. Date: Oct. 3, 2019

(65) Prior Publication Data
US 2021/0106610 A1 Apr. 15, 2021

(30) Foreign Application Priority Data
Mar. 26, 2018 (EP) .................................... 18305332

(51) Int. Cl.
*A61K 31/715* (2006.01)
*A61P 27/04* (2006.01)
*A61K 9/00* (2006.01)
*A61K 31/737* (2006.01)

(52) U.S. Cl.
CPC .......... *A61K 31/715* (2013.01); *A61K 9/0048* (2013.01); *A61K 31/737* (2013.01); *A61P 27/04* (2018.01)

(58) Field of Classification Search
CPC .. C08H 37/006; A61K 31/715; A61K 31/737; A61K 9/0048
See application file for complete search history.

(56) References Cited

FOREIGN PATENT DOCUMENTS

| CN | 104055729 A | 9/2014 | |
|---|---|---|---|
| FR | 2981847 A1 * | 5/2013 | ............... A61K 8/73 |
| WO | 2017/134352 A1 | 8/2017 | |

OTHER PUBLICATIONS

Delbarre-Ladrat, C. et al "Bioprospecting for exopolysaccharides from deep-sea hydrothermal vent bacteria . . . " Microorganisms, vol. 5, No. 63, pp. 1-14. (Year: 2017).*
Casillo, A. et al "Exopolysaccharides from marine and marine extremophilic bacteria . . . " Mar. Drugs, vol. 16, No. 2, pp. 1-34. (Year: 2018).*
International Search Report and Written Opinion dated Jun. 19, 2019 in corresponding International Application No. PCT/EP2019/057599; 7 pages.
Kokoulin, Maxim S. et al., "The sulfated O-specific polysaccharide from the marine bacterium *Cobetia pacifica* KMM 3879T", Carbohydrate Research, vol. 387, Jan. 27, 2014, pp. 4-9.
Kokoulin, Maxim S. et al., "The new sulfated O-specific polysaccharide from marine bacterium *Cobetia pacifica* KMM 3878, containing 3,4-O-[(S)-1-carboxyethylidene]-D-galactose and 2,3-O-disulfate-D-galactose", Carbohydrate Research, Pergamon, GB, vol. 397, Jun. 17, 2014, pp. 46-51.
Kokoulin, Maxim S. et al., "Structure and anticancer activity of sulfated O-polysaccharide from marine bacterium *Cobetia litoralis* KMM 3880T", Carbohydrate Polymers, Applied Science Publishers, Ltd. Barking, GB, vol. 154, Aug. 12, 2016, pp. 55-61.

* cited by examiner

*Primary Examiner* — Leigh C Maier
(74) *Attorney, Agent, or Firm* — Maier & Maier, PLLC

(57) ABSTRACT

The use of a polysaccharide derived from a bacterial strain in the prevention of ocular diseases and the treatment of ocular diseases. Especially, the ophthalmic use of a polysaccharide susceptible to be obtained from the CNCM I-5038 *Cobetia marina* bacterial strain in ocular conditions associated with ophthalmic dryness and ophthalmic inflammation.

14 Claims, 2 Drawing Sheets

POLYSACCHARIDES FOR THE TREATMENT OF OCULAR CONDITIONS

FIELD

The present invention relates to the use of a bacterial strain derived polysaccharide in the prevention and the treatment of ocular diseases. More in particular, the invention relates to the ophthalmic use of a polysaccharide (herein P268) susceptible to be obtained from the *Cobetia marina* bacterial strain, filed on 23 Dec. 2015 in the Collection Nationale de Culture de Microorganismes (CNCM—Institut Pasteur 25-28 rue du Docteur Roux—F75724 Paris Ceder 15) under the reference CNCM I-5038, in ocular conditions associated with ophthalmic dryness and inflammation.

BACKGROUND

Polysaccharides are high molecular weight polymers that can either be intracellular or secreted by microorganisms into their environment. The secreted polysaccharides possess physicochemical properties that contribute to the biofilm formation wherein the said microorganism cells adhere one to another and onto a surface as a colony.

Industrial applications of polysaccharides are well known in the art. The most common example of secreted polysaccharides is gellan gum. This polysaccharide is secreted by the thermophilic bacterium *Pseudomonas elodea*. Gellan gum is used in microbial culture media as a substitute of agar polysaccharide but its viscosifying properties have applications in food industry as well. In addition, the use of gellan gum as a viscosifying excipient in ophthalmic compositions is disclosed in CN104055729.

Structural analogies between polysaccharides secreted by microbial strains and the hyaluronic acid have been described in the art.

The Applicant has surprisingly found that the polysaccharide used in the present invention can be used in the prevention and/or the treatment of ocular diseases, e.g., dry eye related symptoms and/or signs of ocular surface damage. These ocular manifestations are often related to diseases such as superficial keratitis, Sjögren's syndrome or primary dry eye syndrome. The compositions of the invention may also be used for the lubrication of the eyes in case of sensation of dryness, burning and ocular fatigue and other minor complaints of no pathological significance induced by dust environmental factors such as smoke, dry heat, air conditioning, wind, cold, extended computer screen use or contact lens.

SUMMARY

This invention thus relates to a composition comprising a polysaccharide for use in the treatment of an eye disease or eye condition. The polysaccharide comprises at least one of each monomer from the group consisting of rhamnose, glucose, galactose, galacturonic acid and N-acetyl-glucosamine monomers. In said polysaccharide from about 10% to about 20% of the hydroxyl groups are sulfated, in weight relative to the total weight of the polysaccharide. Furthermore, the polysaccharide has a molecular weight ranging from about 1,000,000 to about 10,000,000 g/mol.

In one embodiment, in said polysaccharide about 10% of the hydroxyl groups are sulfated, in weight relative to the total weight of the polysaccharide. Furthermore, the polysaccharide has a molecular weight ranging from about 1,000,000 to about 5,000,000 g/mol.

In a second embodiment, said polysaccharide essentially consists of monomers selected from rhamnose, glucose, galactose, galacturonic acid and N-acetyl-glucosamine.

In a preferred embodiment, said polysaccharide presents a composition in weight from about 5% to about 50% of rhamnose, from about 5% to about 50% of glucose, from about 5% to about 40% of galactose, from about 10% to about 50% of galacturonic acid, from about 2% to about 20%, of N-acetyl-glucosamine, with the condition that the sum of the percentages does not exceed 100%.

In an even more preferred embodiment, said polysaccharide presents a composition in weight from about 12% to about 37% of rhamnose, from about 14% to about 40% of glucose, from about 7% to about 30% of galactose, from about 15% to about 43% of galacturonic acid, from about 7% to about 15% of N-acetyl-glucosamine, with the condition that the sum of the percentages does not exceed 100%.

In one embodiment, the polysaccharide is susceptible to be obtained by extraction from the *Cobetia marina* bacterial strain filed on 23 Dec. 2015 in the Collection Nationale de Culture de Microorganismes (CNCM—Institut Pasteur 25-28 rue du Docteur Roux—F75724 Paris Cedex 15) under the reference CNCM I-5038.

The composition for use of the present invention comprises the polysaccharide as previously described in a concentration ranging from 0.001% to 2%, preferably from 0.01% to 1%, more preferably from 0.2% to 0.5%, in weight of the total weight of said composition.

In one embodiment, the composition for use according to the present invention further comprises at least one pharmaceutically acceptable excipient.

The composition for use according to any embodiment of the invention may be in form of eye drops, artificial tears, gel or ointment.

The composition according to the invention is for use in the treatment of an eye disease or eye condition related to an inflammatory condition and/or lesion of the eye. More in particular, the eye disease or eye condition is dry eye condition (keratoconjunctivitis sicca).

In a second aspect, the invention relates to a medicament comprising the composition of the invention.

In a third aspect, the invention relates to multi-dose container including the composition for use of the invention.

In a fourth aspect, the invention relates to a kit including the composition for use of the invention.

DETAILED DESCRIPTION

Figure 1:
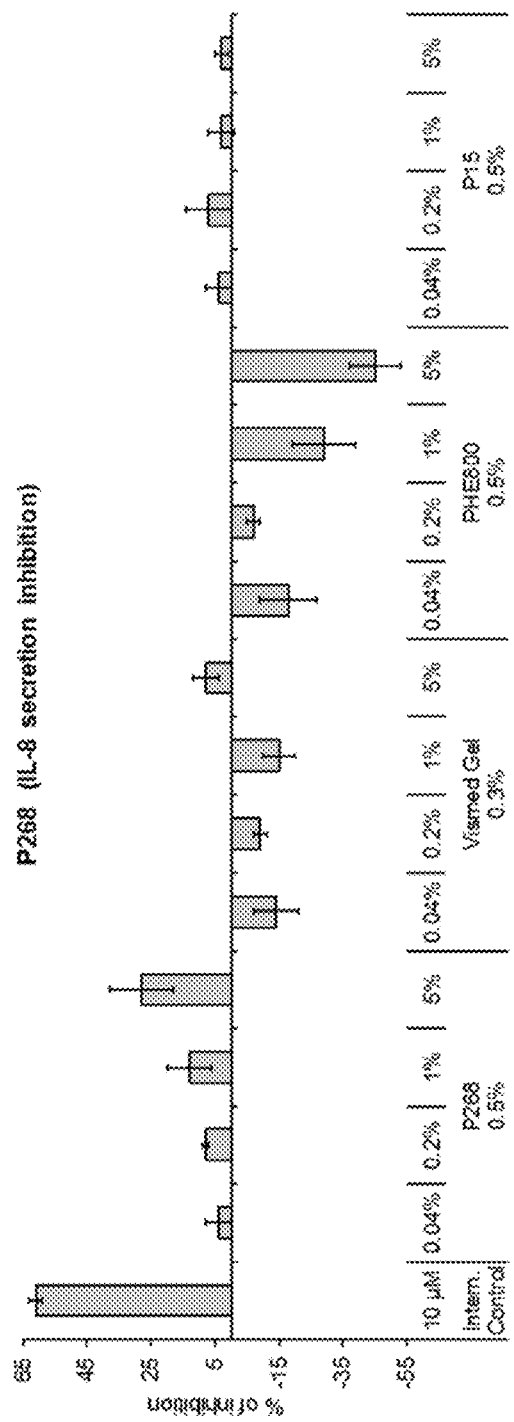
FIG. 1 shows a graph presenting the results of the in vitro inhibition of Interleukin-8 (IL-8) secretion after 48 hours incubation with an internal control compound (Jak inhibitor (Jak inhibitor I; CAS n°457081-03-7) at 10 µM): 0.04%, 0.2%, 1% and 5% dilutions of a P268 0.5% (w/w) solution. The results were compared to those obtained after a 48 hours incubation with 0.04%, 0.2%, 1% and 5% dilutions of a 0.3% (w/w) hyaluronic acid comprising composition (Vismed gel®) as well as with 0.04%. 0.2%, 1% and 5% dilutions of 0.5% (w/w) PHE800 (extracted from *Vibrio diabolicus* CNCM-I-1629 culture, Hyalurift®) and 0.04%, 0.2%, 1% and 5% dilutions of 0.5% (w/w) P15 (Polymaris®) bacterial polysaccharide solutions.

In the present invention, the following terms have the following meanings:

"About" is used herein to mean approximately, roughly, around, or in the region of. When the term "about" is preceding a figure means plus or less 10% of the value of said figure. When the term "about" is used in conjunction with a numerical range, it modifies that range by extending the boundaries above and below the numerical values set forth by 10%.

"Polysaccharide": refers to a polymer compound or preparation containing one or more molecules that contain at least two saccharide molecules (sugar monomers) covalently linked. A polysaccharide may be an intracellular component of a cell or may be secreted to the extracellular environment of a cell. In one embodiment, a polysaccharide can comprise linear sequences of sugar monomers. In another embodiment, the sugar monomers may be linked in a branched way. A "polysaccharide", can be a preparation of molecules that have similar or identical repeating units but different molecular weights within the population. In one embodiment the hydroxyl moieties of the monosaccharides are either participating in the covalent linkages (glycosidic bonds) or are free. In another embodiment, the hydroxyl moieties of the monosaccharides are participating in the covalent linkages (glycosidic bonds), are sulfated or free (i.e., not sulfated). The number of sulfated hydroxyl moieties is expressed as a percentage in weight relative to the total weight of the polysaccharide.

"Pharmaceutically acceptable excipient" refers to a carrier or adjuvant that may be administered to a patient, together with one or more compounds of the present invention, and which does not destroy the pharmacological activity thereof and is nontoxic when administered in doses sufficient to deliver a therapeutic amount of the compound.

This invention relates to a composition comprising a polysaccharide for use in the treatment of an eve disease or eye condition.

The polysaccharide used in the invention's compositions comprises at least one of each monomer from the group consisting of rhamnose, glucose, galactose, galacturonic acid and N-acetyl-glucosamine monomers. Polysaccharide monomeric structure may be determined with routine methods well-known in the art, such as Gas chromatography (GC), Nuclear Magnetic Resonance (NMR) spectroscopy, or mass spectrometry (MS).

In said polysaccharide from about 10% to about 20% of the hydroxyl groups are sulfated, in weight relative to the total weight of the polysaccharide. Rate of sulfated hydroxyl groups may be determined with routine methods well-known in the art, such as High-Performance Liquid Chromatography (HPLC) coupled with amperometry, colorimetry, sulfur elemental analysis or infrared (IR) analysis.

The polysaccharide used in the invention has a molecular weight ranging from about 1,00000 to about 10,000,000 g/mol. Polysaccharide molecular weight may be determined with routine methods well-known in the art, such as size exclusion chromatography (SEC) coupled with light scattering (LS).

According to a first embodiment, the polysaccharide comprises at least one of each monomer from the group consisting of rhamnose, glucose, galactose, galacturonic acid and A-acetyl-glucosamine monomers. In said polysaccharide from about 10% to about 20% of the hydroxyl groups are sulfated, in number of hydroxyl groups relative to the total number of hydroxyl groups of the polysaccharide. The polysaccharide has a molecular weight ranging from about 1,000,000 to about 10,000,000 g/mol.

According to a second embodiment, the polysaccharide comprises at least one of each monomer from the group consisting of rhamnose, glucose, galactose, galacturonic acid and N-acetyl-glucosamine monomers. In said polysaccharide about 10% of the hydroxyl groups are sulfated, in weight relative to the total weight of the polysaccharide. The polysaccharide has a molecular weight ranging from about 1,000,000 to about 5,000,000 g/mol.

In a third embodiment, the polysaccharide, as previously described, essentially consists of monomers selected from rhamnose, glucose, galactose, galacturonic acid and N-acetyl-glucosamine.

According to a fourth embodiment, the polysaccharide, as previously described, presents a composition in weight from about 5% to about 50% of rhamnose, from about 5% to about 50%, of glucose, from about 5% to about 40% of galactose, from about 10% to about 50% of galacturonic acid, from about 2% to about 20% of N-acetyl-glucosamine, with the condition that the sum of the percentages does not exceed 100%.

In a preferred embodiment, the polysaccharide, as previously described, presents a composition in weight from about 12% to about 37% of rhamnose, from about 14% to about 40% of glucose, from about 7% to about 30% of galactose, from about 15% to about 43%, of galacturonic acid, from about 7% to about 15% of N-acetyl-glucosamine, with the condition that the sum of the percentages does not exceed 100%.

In another embodiment, the polysaccharide essentially consists of monomers selected from rhamnose, glucose, galactose, galacturonic acid and N-acetyl-glucosamine wherein the molar ratio of each sugar is as follows:

Rhamnose: 2, 3, or 4;
Glucose: 2, 3, or 4;
Galactose: 1, 2 or 3;
Galacturonic acid: 2, 3, or 4;
N-acetyl-glucosamine: 1.

In a particular embodiment, the polysaccharide is P268 extracted from a culture of a *Cobetia marina* genus bacterial culture. In one embodiment, the polysaccharide is P268 which is extracted from a culture of the *Cobetia marina* genus bacterial culture (also referred as "ENGIE 2-68 PB") deposited by POLYMARIS BIOTECHNOLGY (Aéropôle Centre, 29600 Morlaix, France) in accordance with the Budapest Treaty, on 23 Dec. 2015, in the "Collection Nationale de Culture de Microorganismes" [National Microorganism Culture Collection] (CNCM), Pasteur Institute, 28 rue du Docteur Roux, 75724 Paris, France, under code CNCM I-5038.

In one embodiment, the polysaccharide is susceptible to be obtained by extraction of said polysaccharide from a *Cobetia marina* bacterial strain culture.

In one embodiment, the polysaccharide is susceptible to be obtained by extraction from the *Cobetia marina* bacterial strain filed on 23 Dec. 2015 in the Collection Nationale de Culture de Microorganismes (CNCM—Institut Pasteur 25-28 rue du Docteur Roux—F75724 Paris Cedex 15) under the reference CNCM I-5038.

P268 has a molecular weight ranging from about 1,000,000 to about 10,000,000 g/mol. From about 10% to about 20% of the hydroxyl groups are sulfated, in weight relative to the total weight of the P268 polysaccharide. Furthermore, P268 presents a composition in weight from about 5% to about 50% of rhamnose, from about 5% to about 50% of glucose, from about 5% to about 40% of galactose, from about 10% to about 50% of galacturonic acid, from about 2% to about 20% of N-acetyl-glucosamine, with the condition that the sum of the percentages does not exceed 100%. P268 essentially consists of monomers selected from rhamnose, glucose, galactose, galacturonic acid and N-acetyl-glucosamine wherein the molar ratio of each sugar is as follows:

Rhamnose: 2, 3, or 4;
Glucose: 2, 3, or 4;
Galactose: 1, 2 or 3;
Galacturonic acid: 2, 3, or 4;
N-acetyl-glucosamine: 1.

The *Cobetia marina* strain (also referred as "ENGIE 2-68 PB") which produces the polysaccharide of this invention was deposited by POLYMARIS BIOTECHNOLOGY (Aéropôle Centre, 29600 Morlaix, France) in accordance with the Budapest Treaty, on 23 Dec. 2015, in the "Collection Nationale de Culture de Microorganismes" [National Microorganism Culture Collection] (CNCM), Pasteur Institute, 28 rue du Docteur Roux, 75724 Paris, France, under the reference CNCM I-5038.

The polysaccharide is extracted from the strain culture by any possible means known in the art. In one embodiment, the polysaccharide is extracted by centrifugation of the strain culture medium. In another embodiment, the polysaccharide is extracted by centrifugation of the strain culture medium followed by microfiltration.

In one embodiment, the composition of the invention comprises the polysaccharide as previously described in an amount ranging from 0.001% to 2% in weight of the total weight of said composition.

In one embodiment, the composition of the invention comprises the polysaccharide as previously described in an amount ranging from 0.01% to 1% in weight of the total weight of said composition.

In one preferred embodiment, the composition of the invention comprises the polysaccharide as previously described in an amount ranging from 0.2% to 0.5% in weight of the total weight of said composition.

The invention also relates to a composition as previously described, further comprising at least one pharmaceutically acceptable excipient. The said pharmaceutically acceptable excipient is selected from a group of antioxidants, osmotic, viscosity modulator agent, pH-adjusting agent or buffer, preservative, solubilizers, chelating agents. The amount of additives may be calculated by the skilled artisan with respect to the Pharmacopeia and biological criteria.

In one embodiment, the composition according to the invention includes antioxidants selected from the group of vitamin E, sodium bisulfite, sodium metasulfite, sodium thiosulfate anhydrous, citric acid monohydrate, ascorbyl palmitate and ascorbic acid, butylhydroxyltoluene, butylhydroxyanisole, propylgallate, coenzyme Q10 (2,3-dimethoxy-5-methyl-6-decaprenylbenzoquinone), omega-3 fatty acids. These antioxidants can be used solely or in combination. The amount of antioxidant may be calculated by the skilled artisan with respect to the Pharmacopeia criteria and biological criteria.

In one embodiment, the composition of the invention includes at least one osmotic agent selected from the group of glycerol, propylene glycol, sodium chloride, potassium chloride, sorbitol, mannitol, xylitol, erythritol and the like. In certain embodiments, trehalose can be used as osmoprotectant and a stabilizer as well. Also, the amount of osmotic agent is determined in respect of the Pharmacopeia criteria and biological criteria.

In one embodiment, the composition does not comprise a viscosity modulator agent. In another embodiment, the composition includes at least one viscosity modulator agent selected from the group of carbomers, polycarbophil, cellulose derivatives (e.g. hydroxypropylcellule, hydroxypropylmethylcellulose, carboxymethylcellulose . . . ), povidone, copovidone, natural gums gellan gum, guar gum, xanthan gum, agar agar, xyloglucan . . . ), poloxamer and like. These viscosity modulator agents can be used solely or in combination, the amount fulfilling the requirement of the Pharmacopeia (in Europe and in the U.S.) and biological criteria.

In one embodiment, the composition of the invention displays a viscosity superior to 1 Pa·s at very low shear rate (less than 0.1 s$^{-1}$). In one embodiment, the composition of the invention displays a viscosity superior to 1 Pa·s at zero shear rate.

The composition viscosity is measured using a rheometer equipment known by the skilled man of the art (e.g., Rotational rheometer Kinexus, Malvern UK), between 25 and 35° C., at atmospheric pressure (1 atm).

In one embodiment, the composition of the invention is not buffered. In another embodiment the composition of the invention includes at least one pH-adjusting agent or buffer selected from hydrochloric acid, citric acid, phosphoric acid, acetic acid, sodium hydroxide, potassium hydroxide, boric acid, borax, sodium carbonate, sodium hydrogen carbonate, disodium phosphate, tri-sodium phosphate and the like. The amount of pH adjusting agent is function of the final pH value, comprised between 3.5 and 7.5; preferably from about 6.4 to about 7.3. Also, the amount of pH adjusting agent is used in respect of the Pharmacopeia criteria and biological criteria.

In one embodiment, the composition of the invention is preservative-agent-free (or "preservative-free"). In another embodiment, the composition of the invention includes at least one preservative agent selected from benzalkonium chloride (BAK), benzyl alcohol, mercury salts, thiomersal, chlorhexidine, boric acid and/or a salt thereof or the like, as such or in combination. Also, the amount of preservative agent is used in respect of the Pharmacopeia criteria and biological criteria.

In one embodiment, the composition of the invention includes at least one solubilizer selected from ethanol, polyethylene glycol, glycerol, propylene glycol, N-methyl pyrrolidone, glycofurol, dimethyl isosorbide. Also, the amount of solubilizer is used in respect of the Pharmacopeia criteria and biological criteria.

In one embodiment, the composition of the invention includes at least one chelating agent selected from edetic acid and salts thereof, ethylene glycol tetraacetic acid and salts thereof, citric acid, metaphosphoric acid, pyrophosphoric acid, polyphosphoric acid, malic acid, tartaric acid, phytic acid, and salts thereof; more preferably at least one type selected from the group consisting of edetic acid, citric acid, metaphosphoric acid, polyphosphoric acid, and salts thereof; and particularly preferably a salt of edetic acid. Also, the amount of chelating agent is used in respect of the Pharmacopeia criteria and biological criteria.

In one embodiment, the composition of the invention may be sterilized by any method known in the art.

Non-limiting examples of sterilization methods are heating, such as by autoclaving, filtering or filtration, irradiation, and gas sterilization.

In one embodiment de composition of the invention is a solution or an emulsion. In a preferred embodiment the composition is a solution.

The pH of the solution comprising the composition according to the invention ranges from about 4.2 to about 7.4, preferably from about 6.4 to about 7.3.

The osmolarity of the solution comprising the composition according to the invention ranges from about 100 to about 250 mPa·s, preferably from about 170 to about 220 mPa·s.

The viscosity at 25° C. of the solution comprising the composition according to the invention ranges from about 1 to about 70 mPa·s, preferably from about 2 to about 60 mPa·s.

In one embodiment, the composition of the invention may be a liquid, fluid, gel, powder, ointment, cream, patch, film formulation or any delivery formulation suitable for ophthalmic administration.

In a preferred embodiment, the composition of the invention may be in the form of eye drops, artificial tears, gel or ointment.

In one aspect, the invention relates to a medicament comprising the composition of the invention as previously described.

In another aspect, the invention relates to a device that contains or comprises the polysaccharide, the composition or the medicament of the present invention. According to a first embodiment, the device is a container containing the polysaccharide, the composition or the medicament of the present invention. The container may be opened in a way that minimizes and/or inhibits the microbial contamination of the content. The containers nozzle may be suitable for drop instillation the subject's eye. The container may be a single dose container, or a multiple dose container.

In a second embodiment; the device can be any device known in the art for applying and/or injecting. In such embodiment, the device can be a prefilled syringe apparatus.

In one embodiment, the composition of the invention is packaged in unitary doses; in another embodiment, the composition is packaged in suitable multi-dose containers.

In another aspect, the invention relates to a kit comprising the composition or the medicament of the invention as previously described. The kit may comprise a unitary dose form or a multi-dose container of the composition or the medicament of the present invention. The kit may further contain a composition-applying device (e.g., an eye drop dispenser or a syringe) and/or sterile gazes for absorbing the excessive composition remaining in the eye area after the application of the composition.

In the meaning of the invention, eye diseases or eye conditions are dry eye condition such as for example dry-eye syndrome or chronic dry-eye diseases such as keratoconjunctivitis sicca (KCS), atopic keratoconjunctivitis (AKC) and vernal keratoconjunctivitis (VKC), glaucoma, ocular inflammation conditions such as for example keratitis, corneal epithelium erosion, uveitis, including anterior uveitis, intraocular inflammation, allergy and dry-eye syndrome ocular infections, ocular infections, ocular allergies, corneal or conjunctival lesions, cancerous growth, diabetic macular edema, age-related macular degeneration, anesthesia of the cornea or mydriase of the pupil.

In one embodiment, the eye condition may be blepharitis, glaucoma, Meibomian glands disorders such as for example meibomian gland dysfunction (MGD) and dry eye condition such as for example dry-eye syndrome or chronic dry-eye diseases, diabetic keratopathy or neurotrophic keratopathy.

In one embodiment, the condition may be related to demodex folliculorum infection. In one embodiment, the condition is glaucoma. In one embodiment, the condition is anterior uveitis.

In one embodiment, the eye disease or condition is not an ocular proliferative disease, i.e. a proliferative disease that forms in tissues of and around the eye, such as melanoma (in cells that make the pigment melanin in the eye), carcinoma (in tissues which cover structures in the eye), lymphoma (in immune system cells), and retinoblastoma (in the retina). In one embodiment, the eye disease or condition is not an eye cancer.

In another aspect, the compositions of the invention are for use in the manufacture of a medicine or medicament for the treatment of an eye disease or an eye condition.

This invention also relates to a method for the treatment of an eye disease or an eye condition in a subject in need thereof, comprising a step of ocular administration to the eye of the subject of the polysaccharide, the composition or the medicament according to the invention, as previously described.

In one embodiment, the administration is topical. In one embodiment, the administration is intraocular, e.g., intraocular injection.

EXAMPLES

The present invention is further illustrated by the following examples.

Example 1

Polysaccharide P268 Extraction from a CNCM I-5038 Culture

The polysaccharide P268 used in the present invention was obtained from the freeze-dried supernatant of the CNCM I-5038 *Cobetia marina* bacterial strain culture.

The bacterial cell culture was carried-out in a 5 L fermenter containing marine broth medium 2216 (BD Difco) supplemented with glucose (30 g/L) at 25° C. The culture medium was inoculated at 10% (v/v) with a bacterial suspension in the exponential growth phase. The pH was adjusted and maintained at 7.5 by automatic addition of 1 M NaOH. The medium was oxygenated at 15 L/min with an agitation rate of 350 rpm. After 72 h of fermentation, bacterial cells were removed from the culture medium by centrifugation (16,000 g, 30 min). The supernatant, containing the excreted polysaccharide P268, was then purified by ultrafiltration (100 kDa). The P268 sample was freeze-dried and stored at room temperature away from light and moisture.

Example 2

Polysaccharide P268 Structural Analysis

Polysaccharide P268 used in the present invention and manufactured as described in Example 1 above was analysed according to structure determination methods known in the art.

GC Analysis

Monomeric structure of polysaccharide P268 was determined as:

TABLE 1

P268 monomeric mass composition

| Monomer | % w/w |
| --- | --- |
| Rhamnose | 12-37% |
| Glucose | 14-40% |
| Galactose | 7-30% |
| Galacturonic acid | 15-43% |
| N-acetyl-glucosamine | 7-15% |

HPLC-Amperometry Analysis

Sulfated hydroxyl groups rate of polysaccharide P268 was determined as being 10% to 20% w/w of the hydroxyl groups which are sulfated.

SEC-LS Analysis

Molecular weight of polysaccharide P268 was determined as being higher than 1 000 000 g/mol.

Example 3

P268 Solutions Preparation

Concentrated P268 solution was prepared, weighing water and P268 together in a beaker. After storage one night at 25° C., the solution was stirred until full solution homogenization. Three P268 solutions were obtained.

TABLE 2

P268 solutions compositions

|  | Solution 1 | Solution 2 | Solution 3 |
| --- | --- | --- | --- |
| P268 | 0.1 | 0.3 | 0.5 |
| Sodium chloride | 0.6 | 0.6 | 0.6 |
| Water | Qs 100 | Qs 100 | Qs 100 |

The physicochemical properties of the obtained solutions were compared to a 0.18% w/w hyaluronic acid (HA)-comprising composition (Vismed multi®) and are presented in Table 3.

TABLE 3

P268 solutions physicochemical properties compared to a 0.18% w/w hyaluronic acid (HA)-comprising composition

|  | Solution 1 | Solution 2 | Solution 3 | 0.18% HA |
| --- | --- | --- | --- | --- |
| pH | 6.49 | 6.68 | 6.76 | 7.27 |
| Osmolality (mosm/kg) | 195 | 202 | 201 | 154 |
| Viscosity (mPas) at 25° C. | 2.87 | 11.59 | 61.06 | 20.30 |
| Viscosity (mPas) at 37° C. | 2.98 | 7.60 | 35.45 | 13.19 |

Example 4

In Vitro Interleukin-8 (IL-8) Inhibition by P268 and Other Polysaccharides

Keratinocytes (NHEK) were seeded in 96-well plates and cultured in culture medium for 24 hours. The medium was then replaced by culture medium containing or not (control) the test compounds or the reference (Jak inhibitor (Jak inhibitor I; CAS no 457081-03-7) at 10 µM) or the solvent control (PBS at 5%) and the cells were pre-incubated for 24 hours. After the pre-incubation, the cells were treated again with the test compounds, the reference or solvent control and stimulated or not (non-stimulated control) with the mix of cytokines (IL-17+OSM+TNFalpha at 3 ng/ml each). The cells were incubated for 48 hours. All experimental conditions were performed in n=3 except for the stimulated and non-stimulated controls in n=6.

After incubation, the culture supernatants were collected for interleukin-8 (IL-8) release quantification. IL-8 quantification was measured using an ELISA kit (Duo set IL-8, R&D Systems) according to the supplier's specifications. The NHEK viability was evaluated on the cell layers using a standard MTT reduction assay.

As shown in FIG. 1, the cells treated with a 5% dilution of a 0.5% w/w P268 solution (final concentration 0.025% w/w) showed a 30% IL-8 secretion inhibition compared to the Jak inhibitor at 10 µM. P268 inhibited IL-8 secretion inhibition in a dose-dependent manner.

The hyaluronic acid solution (Vismed gel®) inhibited the IL-8 secretion solely at the higher tested concentration. Said inhibition was significantly inferior to the one observed after the P268 treatment.

Not all bacterial polysaccharides possess anti-inflammatory properties. As shown in FIG. 1, the bacterial polysaccharide PHE800 (Hyalurift®) showed no IL-8 secretion inhibition while bacterial polysaccharide P15 (Polymaris®) showed an insignificant IL-8 secretion inhibition compared to P268, under the same experimental conditions. PHE800 and P15 do not fall in the scope of the polysaccharide according to the present invention.

Example 5

Carrageenan-Induced Conjunctivitis Rat Model

Evaluation of the inhibitory effect of P268 on subconjunctival edema formation in the rat model of carrageenan-induced conjunctivitis, with Mucosta, Hyalein, and Proranon (Pranoprofen) as comparators.

TABLE 4

Carrageenan-induced conjunctivitis model assay, treated groups

| Group | Test solution | Dose | Number of animals |
| --- | --- | --- | --- |
| 1 | Vehicle (PBS) | 0% | 8 |
| 2 | P268 | 0.3% | 8 |
| 3 | Mucosta UD2% | 2% | 8 |
| 4 | Hyalein 0.3% | 0.3% | 8 |
| 5 | Proranon 0.1% (positive control) | 0.1% | 8 |
| 6 | Flumetholon 0.1% | 0.1% | 8 |

The test solutions (5 µL/eye) are administered 1 hour before carrageenan administration to Wistar rats. Subsequent administrations are performed at 0, 1, 2, and 3 hour after carrageenan administration. Each test solutions is administered 5 times during the course of the experiment.

Four hours after carrageenan administration, the subconjunctival tissue (with the edematous lesion) is collected and the weight measured. The lower the weight, the better the efficacy.

Figure 2:
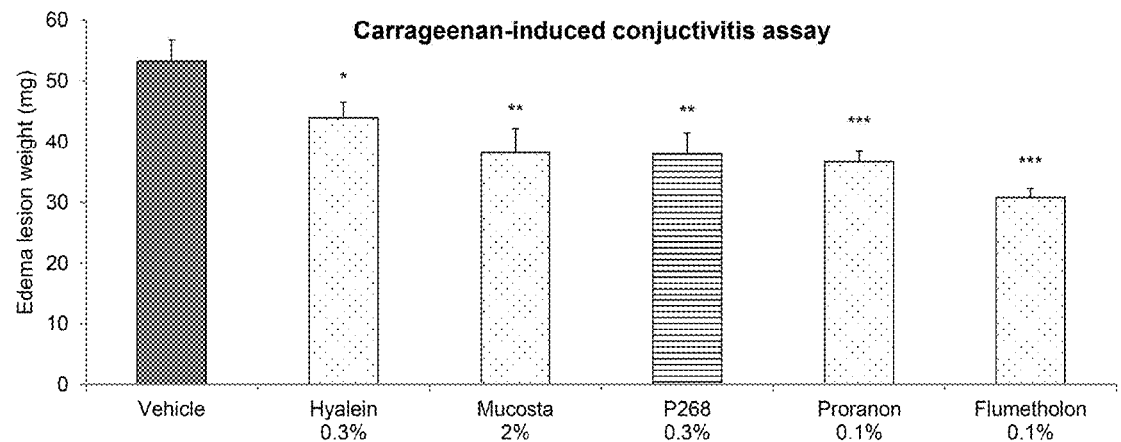
FIG. 2 shows a graph presenting the results of the in vivo Carrageenan-induced conjunctivitis assay. The edema lesion weight (in mg) was measured after treatment with the vehicle, and a 0.3% solution of P268. The results were compared to those obtained after the treatment with Hyalein® 0.3%, Mucosta® %, Propranon® 0.1% and Flumetholon® 0.1%.

The results of the carrageenan-induced conjunctivitis model assay are presented in FIG. 2.

Significant anti-inflammatory effect was observed in the group P268 (0.3%) instillation, as reduction of the edematous lesion weight.

Example 6

Exorbital Lacrimal Gland Excised Dry Eye Rat Model

To evaluate the inhibitory effect of P268 on corneal epithelial damages in the exorbital lacrimal gland excised dry eye disease ("DED") rat model, with Diquas as comparator.

TABLE 5

Exorbital lacrimal gland excised dry eye rat model treated groups.

| Group | Lacrimal gland excision | Test solution | Dose | Number of eyes |
|---|---|---|---|---|
| 1 |   | Vehicle | 0% | 8 |
| 2 | + | Vehicle | 0% | 8 |
| 3 | + | P268 at low dose | 0.03% | 8 |
| 4 | + | P268 at middle dose | 0.1% | 8 |
| 5 | + | P268 at high dose | 0.3% | 8 |
| 6 | + | Diquas | 3% | 8 |

8 weeks after lacrimal gland excision (and dry eye development), the test solutions (5 μL/eye) were administrated 6 times per day for 2 weeks.

The superficial punctate keratitis (SPK-score by fluorescein staining) indicative of corneal epithelial damages, were measured 2 weeks after treatment initiation.

Figure 3:
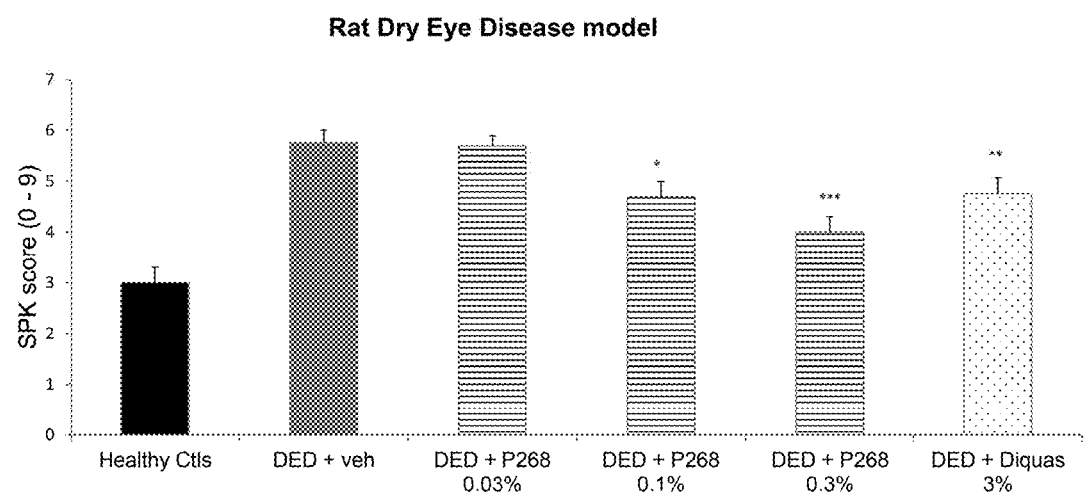
FIG. 3 shows a graph presenting the results of the in vivo rat dry eye ("DED") disease assay by lacrimal gland excision. The Superficial punctate keratitis score ("SPK score") was measured by fluorescein staining in the following groups: Healthy controls, lacrimal gland excised controls treated just with the vehicle of the treatment, lacrimal gland excised treated just with a 0.03% (w/w), a 0.1 (w/w) and a 0.3% (w/w) P268 solution. The results were compared to those of a lacrimal gland excised croup treated with Diquas®3%, solution.

The results of the exorbital lacrimal gland excised dry eye model rat assay are presented in FIG. 3.

Significant inhibitory effect on corneal epithelial damage was observed 2 weeks after the instillation P268 0.1%, P268 0.3% and Diquas.

Example 7

Polysaccharide P268 Ophthalmic Compositions

Ophthalmic compositions including P268 have been manufactured and their physicochemical properties have been studied.

A suitable ophthalmic composition for the topical administration of P268 may be an aqueous formulation, with a physiological pH (about 7) and having an hypoosmolarity of 200 mOsm/kg.

The pH was adjusted by means of a buffer (Tris Buffer 5 mM). Hypoosmolarity was adjusted by means of at least one osmotic agent selected from sodium chloride (NaCl) and sugars (mannitol or trehalose).

pH and rheology (shear viscosity as a function of shear stress) were measured at the following stability points:
T 15 days at 25° C., 40° C., 60° C. and 80° C., and
T 30 days at 25° C., 40° C. and 60° C.
Osmolarity was measured at T 30 days at 25° C.

For each of the compositions 1-4 below, three different concentrations of P268 were tested: 0.1% w/w, 0.3% w/w and 0.5% w/w.

TABLE 6

Ophthalmic compositions of P268

| no | Composition (% w/w) |
|---|---|
| 1 | Tris Buffer 5 mM<br>Mannitol 3.3%<br>Water q.s. 100% |
| 2 | Tris Butler 5 mM<br>NaCl 0.6%<br>Water q.s. 100% |
| 3 | Tris Buffer 5 mM<br>Trehalose 6%<br>Water q.s. 100% |
| 4 | Tris Buffer 5 mM<br>Trehalose 3%<br>NaCl 0.26%<br>Water q.s. 100% | pH generally decreased as a function of temperature, time and P268 concentration, which is more significant at 80° C. The more homogeneous pH stability profiles were obtained for compositions 1 and 2 (containing mannitol or NaCl).

The more homogeneous rheology profiles were obtained for compositions 1 and 2, with a significant superiority for composition 2 (containing NaCl) and more particularly at the concentrations of 0.3% w/w and 0.5% w/w.

No significant variation of osmolarity was observed among compositions 1-4.

Therefore, P268 can be formulated in ophthalmic compositions having the necessary physico-chemical properties for ocular administration.

The invention claimed is:

1. A method for treating an eye disease or eye condition in a subject in need thereof, said method comprising a step of administration of a composition comprising a polysaccharide to said subject,
    wherein said polysaccharide comprises at least one of each monomer selected from the group consisting of rhamnose, glucose, galactose, galacturonic acid and N-acetyl-glucos amine monomers,
    wherein in said polysaccharide from about 10% to about 20% of the hydroxyl groups are sulfated, in weight relative to the total weight of the polysaccharide, and
    wherein said polysaccharide has a molecular weight ranging from about 1,000,000 to about 10,000,000 g/mol.

2. The method according to claim 1, wherein in said polysaccharide about 10% of the hydroxyl groups are sulfated, in weight relative to the total weight of the polysaccharide, and
    wherein said polysaccharide has a molecular weight ranging from about 1,000,000 to about 5,000,000 g/mol.

3. The method according to claim 1, wherein said polysaccharide essentially consists of monomers selected from the group consisting of rhamnose, glucose, galactose, galacturonic acid and N-acetyl-glucosamine.

4. The method according to claim 1, wherein said polysaccharide presents a composition in weight from about 5% to about 50% of rhamnose, from about 5% to about 50% of glucose, from about 5% to about 40% of galactose, from about 10% to about 50% of galacturonic acid, from about 2% to about 20% of N-acetyl-glucosamine, with the condition that the sum of the percentages does not exceed 100%.

5. The method according to claim 1, wherein said polysaccharide presents a composition in weight from about 12% to about 37% of rhamnose, from about 14% to about 40% of glucose, from about 7% to about 30% of galactose, from about 15% to about 43% of galacturonic acid, from about 7% to about 15% of N-acetyl-glucosamine, with the condition that the sum of the percentages does not exceed 100%.

6. The method according to claim 1, wherein said polysaccharide is susceptible to be obtained by extraction of said polysaccharide from the CNCM 1-5038 *Cobetia* marina bacterial strain culture.

7. The method according to claim 1, wherein said composition comprises said polysaccharide in an amount ranging from 0.001% to 2%, in weight of the total weight of said composition.

8. The method according to claim 7, wherein said composition comprises said polysaccharide in an amount ranging from 0.01% to 1%, in weight of the total weight of said composition.

9. The method according to claim 8, wherein said composition comprises said polysaccharide in an amount ranging from 0.2% to 0.5%, in weight of the total weight of said composition.

10. The method according to claim 1, wherein said composition further comprises at least one pharmaceutically acceptable excipient.

11. The method according to claim 1, wherein said composition is in the form of eye drops, artificial tears, gel or ointment.

12. The method according to claim 1, wherein said eye disease or eye condition is an inflammatory condition of the eye.

13. The method according to claim 1, wherein said eye disease or eye condition is a lesion of the eye.

14. The method according to claim 1, wherein said eye disease or eye condition is a dry eye condition (keratoconjunctivitis sicca).

* * * * *